United States Patent
Rigsby et al.

(10) Patent No.: US 9,498,294 B2
(45) Date of Patent: *Nov. 22, 2016

(54) SYSTEMS AND METHODS FOR TAGGING AND TRACKING SURGICAL DEVICES AND SURGICAL ACCESSORIES USING RADIO FREQUENCY IDENTIFICATION TAGS

(71) Applicant: DePuy Synthes Products, Inc., Raynham, MA (US)

(72) Inventors: Christopher Rigsby, Providence, RI (US); Matthew J. Andrie, South Easton, MA (US); Adam LaWare, Medford, MA (US); Timothy A. Beardsley, Kingston, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/878,672

(22) Filed: Oct. 8, 2015

(65) Prior Publication Data

US 2016/0022368 A1    Jan. 28, 2016

Related U.S. Application Data

(63) Continuation of application No. 14/565,613, filed on Dec. 10, 2014, now Pat. No. 9,179,977, which is a continuation of application No. 13/668,645, filed on Nov. 5, 2012, now Pat. No. 8,937,544.

(51) Int. Cl.
*G08B 1/08* (2006.01)
*A61B 19/00* (2006.01)
(Continued)

(52) U.S. Cl.
CPC ............... *A61B 19/44* (2013.01); *A61B 17/70* (2013.01); *A61B 17/7001* (2013.01);
(Continued)

(58) Field of Classification Search
CPC ...................................... G08B 13/14
USPC .................. 340/572.1, 539.12, 572.8, 10.42; 235/385, 487, 492; 600/61; 433/173, 433/174
See application file for complete search history.

(56) References Cited

U.S. PATENT DOCUMENTS 5,633,875 A    5/1997   Hershey et al.
5,996,889 A    12/1999  Fuchs et al.
(Continued)

FOREIGN PATENT DOCUMENTS

EP    2 276 001 A1    1/2011
EP    2 313 019 A1    4/2011
(Continued)

OTHER PUBLICATIONS

[No Author Listed] Tego Applications: New applications: same infrastructure, copyright 2012, accessed Oct. 19, 2012 at <http://www.tegoinc.com/applications/applications.php> (1 page).
(Continued)

*Primary Examiner* — Brent Swarthout
(74) *Attorney, Agent, or Firm* — Nutter McClennen & Fish LLP

(57) ABSTRACT

Various systems and methods are provided for tagging and tracking surgical devices using radio frequency identification (RFID) tags. In general, the systems and methods allow for tracking surgical devices throughout distribution and sterilization thereof. In an exemplary embodiment, the system includes a tray configured to seat a plurality of surgical devices and having a parent RFID tag attached thereto that contains information and/or facilitates access to information about the tray and each of the surgical devices seated therein. Each of the surgical devices seated in the instrument tray can have attached thereto a child RFID tag containing information and/or facilitating access to information about the surgical device.

16 Claims, 10 Drawing Sheets

(51) Int. Cl.
    *G08B 13/24*     (2006.01)
    *A61B 17/70*     (2006.01)
    *A61L 2/00*     (2006.01)
    *A61L 2/26*     (2006.01)

(52) U.S. Cl.
    CPC .............. *A61B 50/20* (2016.02); *A61B 50/22* (2016.02); *A61B 50/30* (2016.02); *A61B 50/33* (2016.02); *A61B 50/34* (2016.02); *A61B 90/40* (2016.02); *A61B 90/90* (2016.02); *A61B 90/98* (2016.02); *A61L 2/00* (2013.01); *A61L 2/26* (2013.01); *G08B 13/2462* (2013.01); *A61B 2050/005* (2016.02); *A61B 2050/3008* (2016.02); *A61B 2050/3011* (2016.02); *A61L 2202/21* (2013.01); *A61L 2202/24* (2013.01); *G08B 13/24* (2013.01)

(56) References Cited

U.S. PATENT DOCUMENTS

| | | | |
|---|---|---|---|
| 6,223,137 B1 | 4/2001 | McCay et al. | |
| 6,861,954 B2 | 3/2005 | Levin | |
| 7,118,029 B2 | 10/2006 | Nycz et al. | |
| 7,142,118 B2 | 11/2006 | Hamilton et al. | |
| 7,213,767 B2 | 5/2007 | Tethrake et al. | |
| 7,227,469 B2 | 6/2007 | Varner et al. | |
| 7,253,736 B2 | 8/2007 | Tethrake et al. | |
| 7,256,699 B2 | 8/2007 | Tethrake et al. | |
| 7,268,684 B2 | 9/2007 | Tethrake et al. | |
| 7,269,476 B2 | 9/2007 | Ratnakar | |
| 7,286,900 B1 | 10/2007 | Frederick et al. | |
| 7,317,393 B2 | 1/2008 | Maloney | |
| 7,362,228 B2 | 4/2008 | Nycz et al. | |
| 7,492,261 B2 | 2/2009 | Cambre et al. | |
| 7,518,502 B2 | 4/2009 | Austin et al. | |
| 7,568,619 B2 | 8/2009 | Todd et al. | |
| 7,675,421 B2 | 3/2010 | Higham | |
| 7,701,334 B1 | 4/2010 | Perkins et al. | |
| 7,752,085 B2 | 7/2010 | Monroe | |
| 7,774,244 B2 | 8/2010 | Kreiner et al. | |
| 7,775,056 B2 | 8/2010 | Lowenstein | |
| 7,868,754 B2 | 1/2011 | Salvat, Jr. | |
| 7,990,272 B2 | 8/2011 | Wass et al. | |
| 8,020,768 B2 | 9/2011 | Ramos-Elizondo et al. | |
| 8,042,738 B2 | 10/2011 | Cloix | |
| 8,113,424 B2 | 2/2012 | Philippe | |
| 8,937,544 B2 | 1/2015 | Rigsby et al. | |
| 9,179,977 B2 * | 11/2015 | Rigsby et al. | 340/572.1 |
| 2004/0150525 A1 | 8/2004 | Wilson et al. | |
| 2005/0012617 A1 * | 1/2005 | DiSilvestro ............... A61F 2/32 | 340/572.8 |
| 2005/0062603 A1 | 3/2005 | Fuerst et al. | |
| 2005/0068182 A1 * | 3/2005 | Dunlap ................... B29C 45/14 | 340/572.8 |
| 2005/0102167 A1 | 5/2005 | Kapoor | |
| 2006/0006999 A1 | 1/2006 | Walczyk et al. | |
| 2006/0043177 A1 | 3/2006 | Nycz et al. | |
| 2006/0109105 A1 | 5/2006 | Varner et al. | |
| 2006/0109118 A1 | 5/2006 | Pelo et al. | |
| 2006/0119481 A1 | 6/2006 | Tethrake et al. | |
| 2006/0145856 A1 | 7/2006 | Tethrake et al. | |
| 2006/0186210 A1 | 8/2006 | Tethrake et al. | |
| 2006/0214791 A1 | 9/2006 | Tethrake et al. | |
| 2006/0232408 A1 | 10/2006 | Nycz et al. | |
| 2006/0235488 A1 | 10/2006 | Nycz et al. | |
| 2006/0244593 A1 | 11/2006 | Nycz et al. | |
| 2006/0244597 A1 | 11/2006 | Tethrake et al. | |
| 2006/0244652 A1 | 11/2006 | Tethrake et al. | |
| 2006/0288095 A1 | 12/2006 | Torok et al. | |
| 2007/0001839 A1 | 1/2007 | Cambre et al. | |
| 2007/0080223 A1 | 4/2007 | Japuntich | |
| 2007/0112649 A1 | 5/2007 | Schlabach | |
| 2007/0125392 A1 | 6/2007 | Olson et al. | |
| 2007/0139202 A1 | 6/2007 | Austin | |
| 2007/0159336 A1 | 7/2007 | Tethrake et al. | |
| 2007/0159337 A1 | 7/2007 | Tethrake et al. | |
| 2007/0188306 A1 | 8/2007 | Tethrake et al. | |
| 2007/0222599 A1 | 9/2007 | Coveley et al. | |
| 2007/0239289 A1 | 10/2007 | Cambre et al. | |
| 2007/0244470 A1 | 10/2007 | Barker, Jr. et al. | |
| 2007/0272746 A1 | 11/2007 | Ortiz et al. | |
| 2007/0273517 A1 | 11/2007 | Govind | |
| 2008/0030345 A1 | 2/2008 | Austin et al. | |
| 2008/0255556 A1 | 10/2008 | Berger | |
| 2008/0270178 A1 | 10/2008 | McRae et al. | |
| 2008/0296373 A1 | 12/2008 | Zmood et al. | |
| 2008/0316045 A1 | 12/2008 | Sriharto et al. | |
| 2009/0021345 A1 | 1/2009 | Sriharto et al. | |
| 2009/0099862 A1 | 4/2009 | Fireman et al. | |
| 2009/0155744 A1 * | 6/2009 | Jandali ..................... A61C 8/00 | 433/174 |
| 2009/0182582 A1 | 7/2009 | Hammon | |
| 2009/0266728 A1 | 10/2009 | Turner et al. | |
| 2010/0036755 A1 | 2/2010 | Saghbini | |
| 2010/0096454 A1 | 4/2010 | Cloix | |
| 2010/0108761 A1 | 5/2010 | Nycz et al. | |
| 2010/0141457 A1 | 6/2010 | Wass et al. | |
| 2010/0252626 A1 | 10/2010 | Elizondo et al. | |
| 2010/0253506 A1 | 10/2010 | Teran-Matus et al. | |
| 2011/0114514 A1 | 5/2011 | Bagozzi et al. | |
| 2011/0148624 A1 | 6/2011 | Eaton et al. | |
| 2011/0181394 A1 | 7/2011 | Blair | |
| 2011/0285536 A1 | 11/2011 | Sriharto et al. | |
| 2012/0001750 A1 * | 1/2012 | Monroe ................. A61M 5/002 | 340/539.11 |
| 2012/0025985 A1 | 2/2012 | Bolander et al. | |
| 2012/0044054 A1 | 2/2012 | Hussain et al. | |
| 2013/0061863 A1 * | 3/2013 | Grey .................. B65D 81/3205 | 132/200 |
| 2013/0105577 A1 | 5/2013 | Hildreth et al. | |
| 2013/0140367 A1 * | 6/2013 | Binmore .......... G06K 19/07779 | 235/492 |
| 2014/0125482 A1 | 5/2014 | Rigsby et al. | |
| 2015/0091725 A1 | 4/2015 | Rigsby et al. | |

FOREIGN PATENT DOCUMENTS

| | | |
|---|---|---|
| EP | 1 835 862 B1 | 6/2011 |
| WO | 2004/008387 A1 | 1/2004 |
| WO | 2005/066871 A2 | 7/2005 |
| WO | 2006/026225 A1 | 3/2006 |
| WO | 2006/026246 A1 | 3/2006 |
| WO | 2006/026289 A1 | 3/2006 |
| WO | 2006/060261 A2 | 6/2006 |
| WO | 2006/063103 A2 | 6/2006 |
| WO | 2006/073849 A1 | 7/2006 |
| WO | 2006/091797 A1 | 8/2006 |
| WO | 2006/113660 A1 | 10/2006 |
| WO | 2006/115958 A1 | 11/2006 |
| WO | 2010/042849 A1 | 4/2010 |
| WO | 2010/102069 A2 | 9/2010 |
| WO | 2011/084435 A2 | 7/2011 |

OTHER PUBLICATIONS

[No Author Listed] Tego Applications: RFID that survives gamma sterilization, copyright 2012, accessed Oct. 19, 2012 at <http://www.tegoinc.com/applications/applications_gamma.php> (1 page).

[No Author Listed] Tego Products: Rugged industrial high-memory tags, copyright 2012, accessed Oct. 19, 2012 at <http://www.tegoinc.com/products/products_tegotag.php> (2 pages).

[No Author Listed] Tego Products: TegoChipTM—Rugged High-Memory RFID, copyright 2012, accessed Oct. 19, 2012 at <http://www.tegoinc.com/products/products_tegochip.php> (2 pages).

(56) References Cited

OTHER PUBLICATIONS

[No Author Listed] "Vizinex RFID Introduces Sentry-AST Long Range Durable Asset Tag for Outdoor and Industrial Monitoring," Jul. 24, 2012 (2 pages).

[No Author Listed] Xerafy Product Guide, Version No. 9.10.12, accessed Nov. 3, 2012 at <http://www.xerafy.com/userfiles/uploads/brochures/Xerafy-Product-Guide-en.pdf> (2 pages).

International Search Report for Application No. PCT/US2013/068382 mailed Feb. 14, 2014 (4 Pages).

\* cited by examiner

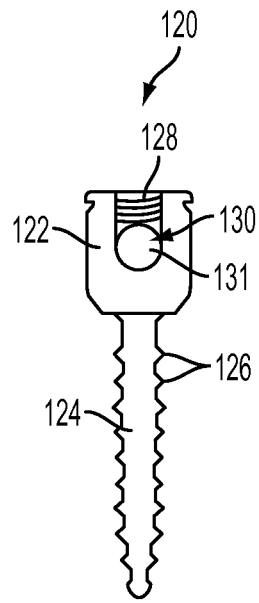  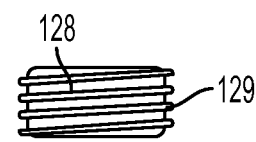
FIG. 3A  FIG. 3B  FIG. 3C
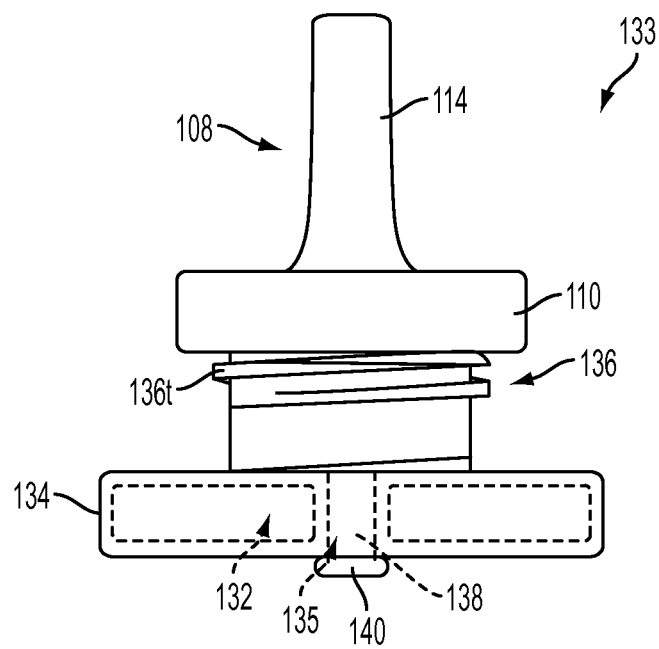
FIG. 4

SYSTEMS AND METHODS FOR TAGGING AND TRACKING SURGICAL DEVICES AND SURGICAL ACCESSORIES USING RADIO FREQUENCY IDENTIFICATION TAGS

CROSS-REFERENCE TO RELATED APPLICATIONS

This application is a continuation of U.S. application Ser. No. 14/565,613 now U.S. Pat. No. 9,179,977 filed on Dec. 10, 2014 and entitled "Systems and Methods for Tagging and Tracking Surgical Devices and Surgical Accessories Using Radio Frequency Identification Tags," which is a continuation of U.S. application Ser. No. 13/668,645 now U.S. Pat. No. 8,937,544 filed on Nov. 5, 2012 and entitled "Systems and Methods for Tagging and Tracking Surgical Devices and Surgical Accessories Using Radio Frequency Identification Tags," each of which is hereby incorporated by reference in its entirety.

FIELD

The present disclosure relates generally to systems and methods for tagging and tracking surgical devices and surgical accessories using radio frequency identification tags.

BACKGROUND

A traditional model for managing distribution of surgical devices and surgical accessories includes several phases. These phases typically include inventory management, surgical preparation, and post-surgery inventory management.

During the inventory management phase, a representative of a medical device company orders various medical devices believed to be necessary for a particular surgery. The ordered medical devices are each labeled with an identifier, such as a stock-keeping unit (SKU) number, a lot number, and/or a serial number. All of the ordered medical devices can be packaged into a carrying tray, which can also be labeled with its own identifier, and shipped to the representative from the medical device company or a distributor affiliated therewith. The identifiers of the ordered medical devices and/or the carrying tray can be logged prior to shipment, thereby allowing the medical device company or the distributor to track which medical devices and/or carrying trays have been shipped.

During the surgical preparation phase, the representative can ensure that all of the necessary devices are present in the tray. The instrument tray can be transferred to a hospital processing center, where the tray can be sterilized and prepared for surgery.

After the surgery, the representative identifies and manually documents the inventory that was consumed, including details of the surgery, e.g., date, time, and a name of a surgeon who performed the surgery. The representative obtains a purchase order from the hospital staff so that a seller, e.g., a surgical device company, can bill for the consumed inventory. The representative also ensures that consumed inventory is replenished and that reusable medical devices are either returned to the medical device company or distributor or are prepared for subsequent use at the hospital.

There are a number of inefficiencies associated with existing distribution management models. For example, the representative spends a significant amount of time manually inspecting each surgical set and completing the accompanying paperwork. This time could be better spent supporting more complex surgeries in which representative input is crucial, or generating new business for the medical device company. Furthermore, there are significant costs associated with employing a large staff of representatives. For another example, it takes a significant amount of time to log ordered medical devices and carrying trays prior to shipment and to log medical devices and carrying trays returned after surgery. Precise tracking is necessary for, e.g., inventory management and accurate billing, but the monetary and time costs of conventional tracking methods are high.

In addition to being inefficient, conventional distribution management systems are subject to inaccuracy due to human error in manually tracking and comparing identifiers. Each identifier has to be individually checked, e.g., scanned with a bar code reader or manually written down, etc. If any one identifier is accidentally missed or inaccurately recorded, inventory cannot be properly managed. Additionally, during shipment, identifiers can be damaged, such as with torn packaging, which can render the identifiers useless.

Additionally, at least some conventional identifiers traditionally cannot undergo repeated sterilization because the intensity of the sterilization, e.g., extreme heat, damages the identifiers and/or causes them to unattach, e.g., by unsticking, from packaging. This necessitates replacement of identifiers for medical devices and carrying trays and returned to the medical device company or its distributor. Such replacement increases costs.

Accordingly, there remains a need for tagging and tracking surgical devices and surgical accessories.

SUMMARY

The present invention generally provides systems and methods for tagging and tracking surgical devices and surgical accessories using radio frequency identification tags. In one aspect, a medical system is provided that includes a surgical device carrying apparatus configured to be transported between an inventory storage location at which surgical inventory is stored and a medical care facility at which surgical procedures are performed, a plurality of surgical devices seated in the surgical device carrying apparatus and being configured to be transported in the surgical device carrying apparatus between the inventory storage location and the medical care facility, a parent radio frequency identification (RFID) tag attached to the surgical device carrying apparatus uniquely identifying the surgical device carrying apparatus and being configured to allow unique identification of each of the plurality of surgical devices seated in the surgical device carrying apparatus, and a plurality of child RFID tags. Each of the child RFID tags uniquely identifies one of the plurality of surgical devices, each of the child RFID tags is configured to be sterilized a plurality of times, and the parent RFID tag is configured to be sterilized a plurality of times.

The child RFID tags can be attached to the plurality of surgical devices in a variety of ways. Each of the child RFID tags can be directly attached to the one of the plurality of surgical devices that the child RFID tag uniquely identifies. Each of the child RFID tags can be removably attached to the one of the plurality of surgical devices that the child RFID tag uniquely identifies.

The parent RFID tag can be attached to the surgical device carrying apparatus in a variety of ways. The parent RFID tag can be directly attached to the surgical device carrying apparatus. The parent RFID tag can be embedded within the surgical device carrying apparatus.

The medical system can include a plurality of lids. Each of the plurality of lids can be removably coupled to the surgical device carrying apparatus such that each of the plurality of lids can be removed from the surgical device carrying apparatus independent of each other. Each of the plurality of lids can be associated with one of the plurality of surgical devices and can be configured to prevent removal of the one of the plurality of surgical devices from the surgical device carrying apparatus until removed from the surgical device carrying apparatus. Each of the plurality of child RFID tags can be attached to one of the plurality of lids such that removing one of the plurality of lids from the surgical device carrying apparatus removes the child RFID attached thereto from the surgical device carrying apparatus and allows the surgical device associated with the removed lid to be removed from the surgical device carrying apparatus.

The plurality of surgical devices can include at least one surgical implant configured to be implanted in a patient and/or at least one surgical tool configured to be used in performing a surgical procedure on a patient. The at least one surgical implant can include a bone anchor having a recess formed therein the, and the child RFID tag for the bone anchor can be attached to the bone anchor by being seated in the recess.

In another aspect, a medical method is provided that includes sterilizing a surgical device carrying apparatus seating a plurality of surgical devices, the surgical device carrying apparatus having a parent RFID tag attached thereto that uniquely identifies the surgical device carrying apparatus and that allows unique identification of each of the plurality of surgical devices, and each of plurality of surgical devices having a child RFID tag attached thereto that uniquely identifies the one of the plurality of surgical devices to which the child RFID tag is attached. After the sterilizing, the surgical device carrying apparatus can be received after a use of the surgical device carrying apparatus. After the receiving, the parent RFID tag and the child RFID tags of any of the surgical devices remaining in the surgical device carrying apparatus can be scanned using an RFID tag reading device. The medical method can also include determining if any one or more of the plurality of surgical devices have been removed from the surgical device carrying apparatus based at least in part on the scanning of the parent RFID tag and the child RFID tags of any of the surgical devices remaining in the surgical device carrying apparatus, and replacing in the surgical device carrying apparatus the determined one or more of the plurality of surgical devices with one or more replacement surgical devices. Each of the one or more replacement surgical devices can have a child RFID tag attached thereto that uniquely identifies the one of the replacement surgical devices to which the child RFID tag is attached. After the determining and the replacing, the surgical device carrying apparatus can be resterilized with the surgical carrying apparatus having the parent RFID tag attached thereto, having the non-removed plurality of surgical devices seated therein with their associated child RFID tags attached thereto, and having the one or more replacement surgical devices seated therein with their associated child RFID tags attached thereto. The sterilizing, receiving, scanning, determining, replacing, and resterilizing can be repeated a plurality of additional times. The use of the surgical device carrying apparatus can include at least one of a transport of the surgical device carrying apparatus from a first geographic location to a second geographic location that is different from the first geographic location, and presence of the surgical device carrying apparatus in a setting of a surgical procedure during which one or more of the plurality of surgical devices is configured to be used.

In another embodiment, a medical method is provided that includes scanning a parent RFID tag attached to a surgical device carrying apparatus seating a plurality of surgical devices, the parent RFID tag uniquely identifying the surgical device carrying apparatus and allowing unique identification of each of the plurality of surgical devices seated in the surgical device carrying apparatus. A plurality of child RFID tags can be scanned, each of the child RFID tags uniquely identifying one of the plurality of surgical devices. After scanning the parent RFID tag and the plurality of child RFID tags, the surgical device carrying apparatus can be sterilized, the surgical device carrying apparatus having the parent RFID tag attached thereto and having the plurality of surgical devices seated therein with the child RFID tags attached thereto. After sterilizing the surgical device carrying apparatus, the parent RFID tag attached to the surgical device carrying apparatus can be rescanned. The method can also include determining, based at least in part on the rescanning of the parent RFID tag, which of the plurality of surgical devices remain seated in the surgical device carrying apparatus. The scanning, sterilizing, rescanning, and determining can be repeated a plurality of additional times.

After determining which of the plurality of surgical devices remain seated in the surgical device carrying apparatus, the surgical device carrying apparatus can be restocked to replace any of the plurality of surgical devices not remaining seated in the surgical device carrying apparatus. Each of the restocked surgical devices can have attached thereto a child RFID tag uniquely identifying the restocked surgical device to which the child RFID is attached. The method can also include causing the parent RFID tag to allow unique identification of each of the one or more restocked surgical devices. The surgical device carrying apparatus can be resterilized, the surgical device carrying apparatus having the parent RFID tag attached thereto, having the remaining plurality of surgical devices seated therein with the child RFID tags attached thereto, and having the restocked surgical devices seated therein with the child RFID tags attached thereto. After resterilizing, the parent RFID tag attached to the surgical device carrying apparatus can be rescanned. The method can further include determining, based at least in part on the rescanning of the parent RFID tag, which of the remaining plurality of surgical devices and the restocked surgical devices remain seated in the surgical device carrying apparatus.

After scanning the parent RFID tag and the plurality of child RFID tags, the surgical device carrying apparatus having the plurality of surgical devices seated therein can be transported from a first location to a second location. The surgical device carrying apparatus having the parent RFID tag attached thereto and having the plurality of surgical devices seated therein with the child RFID tags attached thereto can be sterilized at the second location. The surgical device carrying apparatus and each of the plurality of surgical devices remaining in the surgical device carrying apparatus can be transported from the second location to the first location. The parent RFID tag attached to the surgical device carrying apparatus and each of the child RFID tags remaining in the surgical device carrying apparatus can be rescanned at the second location. The scanning, sterilizing, rescanning, and determining can be repeated a plurality of additional times. The surgical device carrying apparatus can be transported from the first location after each of the repeated scannings.

BRIEF DESCRIPTION OF DRAWINGS

This invention will be more fully understood from the following detailed description taken in conjunction with the accompanying drawings, in which:

FIG. 3A is a side view of a spinal anchor assembly that includes the spinal anchor of FIG. 1;

FIG. 3B is a perspective view of a set screw of the spinal anchor assembly of FIG. 3A;

FIG. 3C is a side view of the set screw of FIG. 3B;

FIG. 4 is a side view of one of the child RFID tag assemblies of FIG. 1;

DETAILED DESCRIPTION

Figure 1:
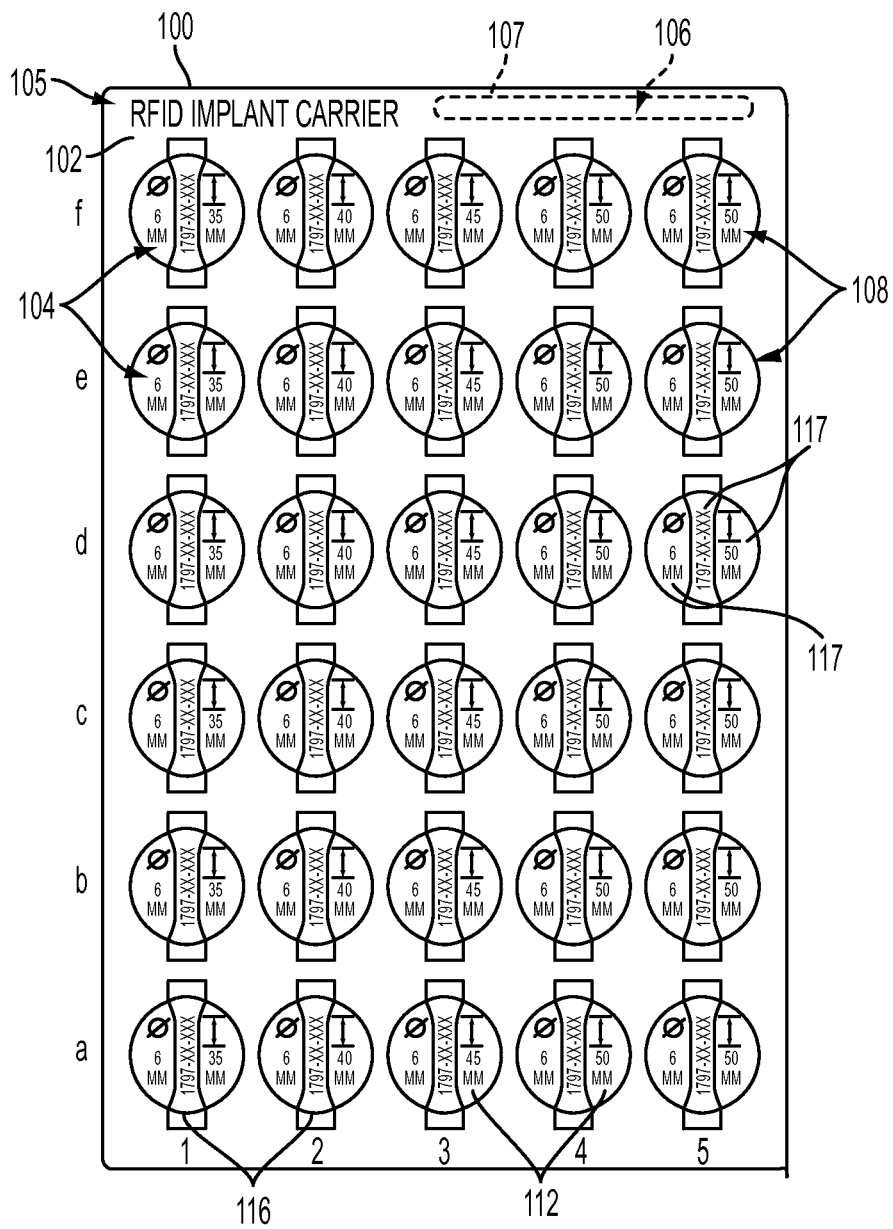
FIG. 1 is a top view of one embodiment of an implant tray having a plurality of spinal anchors seated therein, each of the spinal anchors having an RFID tag assembly attached thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Various systems and methods are disclosed for tagging and tracking surgical devices and surgical accessories using radio frequency identification (RFID) tags. In general, the systems and methods allow for tracking surgical devices and surgical accessories, collectively referred to herein as "surgical devices," throughout distribution and sterilization thereof. In an exemplary embodiment, the system includes a surgical device carrying apparatus, also referred to herein as an instrument tray, an implant tray, and a tray, configured to seat a plurality of surgical devices, which can be same or different from one another. A parent RFID tag containing information and/or facilitating access to information about the tray and each of all the surgical devices stored in the tray can be attached to the tray. In addition, each of the surgical devices seated in the tray can have attached thereto a child RFID tag containing information and/or facilitating access to information about the surgical device to which the child RFID tag is attached. RFID tags can be quickly scanned, such as manually, or automatically, e.g., using an external reading device mounted to an tray conveyer belt, thus increasing the efficiency of surgical device distribution. Identifying trays and surgical devices using RFID tags can allow surgical devices missing from the tray to be identified at any time by comparing information gathered as a result of a scan of the parent RFID tag attached to the tray to information gathered as a result of a scan of all the child RFID tags attached to surgical devices seated within the tray, if any. Comparison of the parent RFID tag's associated information about the surgical devices with the child RFID tags' associated information about their respective surgical devices can be manual, but in an exemplary embodiment the comparison can be automated, which can further enhance the efficiency of the comparison. In an exemplary embodiment, the parent RFID tag and the child RFID tags can be configured to be sterilized multiple times while maintaining their functionality, thereby allowing the tray to be repeatedly used to carry surgical devices between geographic locations and/or allowing unused surgical devices to remain in the tray through multiple shipping cycles, thus saving time and labor. The parent RFID tag and the child RFID tags can be configured to be reprogrammed any number of times to identify different surgical devices through multiple distribution cycles. Thus, the parent RFID tag can remain permanently attached to the tray as different surgical devices are seated within the tray, and/or the child RFID tags can be reused to identify different surgical devices. The parent RFID tag can be directly attached to the tray, e.g. embedded therein, thus helping to prevent accidental detachment of the parent RFID tag from the tray. The child RFID tags can be attached to their respective surgical devices using one or more features of the surgical devices themselves, such as recesses or threads formed on the surgical devices, which can allow the child RFID tags to be attached to surgical devices without using packaging wrapped around or otherwise adhered to the surgical devices, thus saving money and physical resources.

FIG. 1 illustrates one exemplary embodiment of an implant tray 100 configured to seat a plurality of surgical devices therein. The surgical devices seated in the implant tray 100 in FIG. 1 include a plurality of bone anchors, e.g., spinal anchors, obscured in FIG. 1 but shown in FIGS. 3 and 6. However, as discussed further below, the implant tray 100, as well as other embodiments of trays discussed herein, can be configured to seat any kind of surgical device, or any combination of same and/or different surgical devices.

Figure 2:
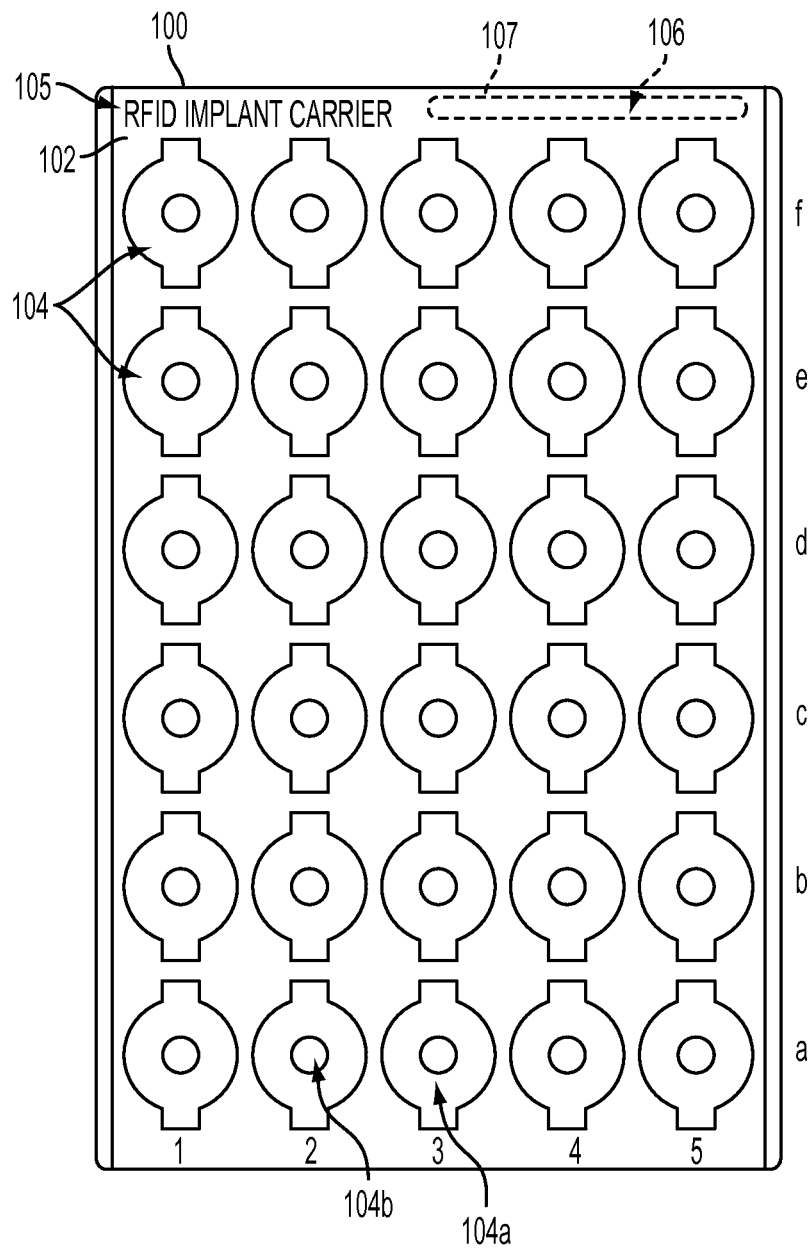
FIG. 2 is a top view of the implant tray of FIG. 1 without the spinal anchors seated therein.

The implant tray 100, shown in FIG. 2 without any surgical devices seated therein, can have a variety of sizes, shapes, and configurations. It will be appreciated by a person skilled in the art that the implant tray 100 shown in FIGS. 1 and 2 is an illustrative, non-limiting example of an implant tray that can be used to seat surgical devices and have a parent RFID tag attached thereto. Other trays illustrated herein are similarly non-limiting examples. Trays which are configured to retain specific surgical devices and/or accessories are typically custom designed by a manufacturer of the devices and/or accessories.

The tray 100 can have a top panel 102 with a plurality of recesses 104 formed therein. Each of the recesses 104 can be configured to seat a surgical device such that the tray 100 can seat a plurality of surgical devices. The recesses 104 can have a variety of sizes, shapes, and configurations, but can generally be configured to securely, safely seat a surgical device therein. In the illustrated embodiment, each of the recesses 104 is configured to seat one spinal anchor, but each of the recesses 104 can be configured to seat any number of surgical devices and other types of surgical devices, the same or different from any other recesses 104 in the tray 100. Each of the recesses 104 can include a top recess 104a and a bottom recess 104b. The top and bottom recesses 104a, 104b can each have a size, e.g., a diameter, a depth, etc., corresponding to a portion of the surgical device to be seated therein and can be arranged in the tray 100 in any way. As shown in the illustrated embodiment, the recesses 104 can be arranged in a plurality of parallel, linear rows a, b, c, d, e, f and a plurality of parallel, linear columns 1, 2, 3, 4, 5. As will be appreciated by a person skilled in the art, the recesses 104 can be configured to receive surgical devices therein in any orientation.

The tray 100 can be labeled with one or more items of information 105 in text and/or graphical format, such as names of surgical devices to be seated therein, to help facilitate use of the tray 100 and/or to help allow for manual inspection of the information 105. The tray 100 can be constructed of any one or more materials, as will be appreciated by a person skilled in the art, such as material(s) that are configured to undergo sterilization and to support a weight of surgical devices seated therein.

The tray 100 can have a parent RFID tag 107 attached thereto, which can facilitate identification of the tray 100 and any surgical devices seated therein, as mentioned above. The parent RFID tag 107 can be attached to the tray 100 in a variety of ways, as will be appreciated by a person skilled in the art. In an exemplary embodiment, the parent RFID tag 107 can be embedded within the tray 100, which can help prevent damage to the parent RFID tag 107 during transport and during unloading/reloading of the tray 100, and/or can facilitate repeated shipments of the tray 100 between different geographic locations. The parent RFID tag 107 can be embedded within the tray 100 in a variety of ways, such as by being embedded therein during manufacture of the tray 100. As in the illustrated embodiment, the tray 100 can include a cavity 106 formed therein that can be configured to seat the parent RFID tag 107 therein so as to embed the parent RFID tag 107 in the tray 100. The cavity 106 can be formed in the tray 100 in any manner and in any location of the tray 100. The parent RFID tag 107 can optionally be secured in the cavity 106 using an adhesive. The tray 100 can include a "door" or lid (not shown) configured to be selectively opened and closed to allow for selective access to the cavity 106, thus reducing chances of accidental displacement of the parent RFID tag 107 during transportation of the tray 100 and/or allowing for intentional removal of the parent RFID tag 107 from the cavity 106, such as for use of the parent RFID tag 107 with another tray or to replace the parent RFID tag 107 with a newer generation RFID tag. The "door" or lid can therefore allow for removal and replacement of the parent RFID tag 107 contained within the cavity 106. The parent RFID tag 107 can be permanently attached to the tray 100 in a number of other ways, such as by being affixed to an exterior surface thereof with an adhesive.

The parent RFID tag 107 can be attached to the tray 100 in a way that allows the tray 100 to be transported between geographical locations, e.g., between a medical device warehouse and a hospital, without the parent RFID tag 107 being exposed on an exterior surface of the tray 100, and/or without the parent RFID tag 107 being visible to the naked eye, which can help protect the parent RFID tag 107. "Hiding" the parent RFID tag 107 can help prevent damage to the parent RFID tag 107 during transport and during unloading/reloading of the tray 100, and can facilitate repeated shipments of the tray 100 between different geographic locations.

The parent RFID tag 107 can be any of various types of RFID tags. In an exemplary embodiment, the parent RFID tag 107 can be configured to undergo multiple sterilizations without losing data stored thereon and while otherwise maintaining its functionality. The parent RFID tag 107 can thus be repeatedly used with same tray 100 through numerous distribution cycles, thereby saving labor and resources. Non-limiting examples of an RFID tag that can be sterilized multiple times are the Sentry AST™ Autoclave tag available from Vizinex RFID of Quakertown, Pa. and the TegoChip™ available from Tego, Inc. of Waltham, Mass. Non-limiting examples of an RFID tag that can be attached to or embedded in a surgical device are the XS Series of RFID Tags (Dot XS and Dash XS) available from Xerafy of Hong Kong, which are manufactured using a ceramic material and can be attached to or embedded in individual medical devices and/or surgical device carrying apparatuses.

The parent RFID tag 107 can be configured to store information, as will be appreciated by a person skilled in the art. The information can uniquely identify the tray 100, e.g., by identification number, alphanumeric code, etc., and can allow unique identification of each surgical device seated in the tray 100. The parent RFID tag 107 can additionally or alternatively be configured to store information related to the use of the tray 100 and/or any surgical devices seated therein, such as how many times the tray 100 has been sterilized or transported between various geographic locations. The parent RFID tag 107 can be reprogrammable to allow for, e.g., updates to a status of the tray 100, changes in the surgical devices seated in the tray 100, etc., such as in between surgical procedures.

In one embodiment, the parent RFID tag 107 can be configured to allow unique identification of each surgical device by storing a "master" list of surgical device and/or child RFID tag identification numbers, alphanumeric codes, etc. In other words, the RFID tag 107 can be configured to store information uniquely identifying each of the surgical device(s) seated in the tray 100 to which the parent RFID tag 107 is attached. The parent RFID tag 107 locally storing information regarding the surgical device(s) seated in the tray 100 associated with the tag 107 can reduce an amount of equipment needed to identify trays and various devices seated therein, which can help reduce cost. Alternatively or additionally, the parent RFID tag 107 can be configured to allow unique identification of each surgical device by the information uniquely identifying the tray 100 allowing access to externally stored information regarding the surgical device(s). In other words, the RFID tag 107 can be configured to store information that allows unique identification of surgical device(s) without storing, e.g., in the RFID tag's memory," information uniquely identifying each of the surgical device(s), e.g., without storing surgical device and/or child RFID tag identification numbers, alphanumeric codes, etc. For non-limiting example, the information uniquely identifying the tray 107, e.g., an identification number, alphanumeric code, etc., can be looked up in an externally stored database including data regarding a plurality of trays and surgical device(s) seated in each one of the trays. The surgical device(s) associated with the tray 107 can therefore be uniquely identified. As will be appreciated by a person skilled in the art, the externally stored database external to the tray 100 can be located in any one or more storage mechanisms, such as in a desktop computer's memory, a standalone external hard drive, a server's memory, a laptop computer's memory, etc. For another non-limiting example, the information stored in the parent RFID tag 107 can include a direct link to the tray's information stored in the externally stored database. Using a database to store information instead of locally storing information on the parent RFID tag 107 can help reduce a size of the parent RFID tag 107 since the parent RFID tag 107 can have a relatively small memory, which can help make the parent RFID tag 107 easier to attach to the tray 100 and/or help reduce monetary cost of the parent RFID tag 107. Locally storing information in the parent RFID tag 107 and using a database to store the information can provide redundancy, which can help protect against data loss.

As mentioned above, although the tray 100 can be configured to seat any number and any combination of different types of surgical devices, the tray 100 in the illustrated embodiment is configured to seat a plurality of the spinal anchors. FIG. 3A illustrates an exemplary embodiment of a spinal anchor that can be seated in the tray 100 and that can be configured to have a child RFID tag 132 (see FIG. 6) attached thereto. The spinal anchor can include a head 122 and a shank 124 extending distally from the head 122. The spinal anchor can be part of a spinal anchor assembly 120 that also includes a set screw 128 configured to be at least partially seated in the head 122. FIGS. 3B and 3C also illustrate the set screw 128. The head 122 can have a recess 130 formed therein that can be configured to seat a spinal fixation element, e.g., a spinal rod 131. The head 122 can be integral with the shank 124, or the head 122 can be a separate, discrete member configured to seat a proximal end of the shank 124 therein, e.g., as with a polyaxial screw. The shank 124 can have one or more bone-engaging features formed thereon, e.g., a thread 126, configured to secure the shank 124, and hence the spinal anchor assembly 120, to bone. The set screw 128 can have a thread 129 formed thereon configured to threadably engage a corresponding thread (obscured in FIG. 3A) formed on a surface of the recess 130, such that the set screw 128 can be seated at least partially within the head 122. The set screw 128 can thus be configured to secure the spinal rod 131 within the recess 130. It will be appreciated by a person skilled in the art that the spinal anchor assembly 120 is an illustrative, non-limiting example of a spinal anchor assembly and of the various types of surgical devices that can be seated in a tray and can have a child RFID tag attached thereto.

The child RFID tag 132 can be attached to the spinal anchor seated in the tray 100 in a variety of ways. The child RFID tag 132 can be removably attached to the spinal anchor, which can facilitate identification of the spinal anchor, as mentioned above, while allowing for removal of the child RFID tag 132 from the spinal anchor before implantation of the spinal anchor in the body. The removed child RFID tag 132 can then be disposed of or can be retained for use with another surgical device. Similarly, the set screw 128 can have a child RFID tag attached thereto, e.g., as discussed below with reference to FIGS. 12-14. In another embodiment, a child RFID tag can be permanently (e.g., non-removably) attached to a surgical device configured to be seated in a tray. In an exemplary embodiment, a child RFID tag can be removably attached to an implantable surgical device, e.g., the spinal anchor assembly 120, a spinal plate, a bone anchor (e.g., a suture anchor, a spinal anchor, etc.), a surgical staple, a surgical clip, a screw, etc., thereby allowing the child RFID tag to be removed from the implant such that the child RFID tag is not implanted within a patient. Removal of the child RFID tag from the surgical device can indicate that the surgical device was used, thereby allowing a charge for the surgical device to be assessed and billed, e.g., by a medical device company. Conversely, a child RFID tag not being removed from the surgical device can indicate the reverse, that the surgical device was not used such that a customer should not be billed for the surgical device. Similarly, in an exemplary embodiment, a child RFID tag can be permanently attached to a non-implantable surgical device, e.g., a surgical stapler, a retractor, a scalpel, scissors, a trocar, etc., which can allow the child RFID tag to uniquely identify the non-implantable surgical devices through multiple shipping cycles and/or through the device's use in multiple surgical procedures. A child RFID tag can, however, be removably attached to a non-implantable surgical device, which can facilitate billing for used surgical devices, as discussed above.

As shown in FIG. 4, the child RFID tag 132 can be attached to a thumb grip 108 as part of a child RFID tag assembly 133 that can assist in attaching and removing the child RFID tag 132 to and from the spinal anchor. The child RFID tag assembly 133 in the illustrated embodiment is configured to threadably mate with the spinal anchor, as discussed further below, but child RFID tag assemblies can have a variety of configurations configured to removably mate with different surgical devices. For non-limiting example, a child RFID tag assembly configured to removably attach to a bone plate, e.g., a spinal plate, can include a locking ring having a child RFID tag attached thereto, e.g., embedded therein. The locking ring can be configured to be snapped open and closed, similar to a bracelet or a binder ring, such that the locking ring can be selectively inserted through and removed from a bore extending through the bone plate.

Figure 5:
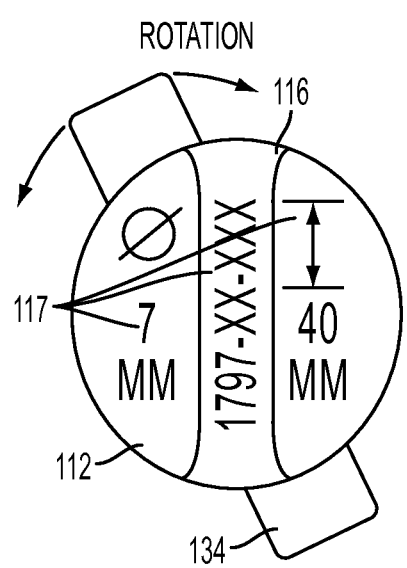
FIG. 5 is a top view of the child RFID tag assembly of FIG. 4.
Figure 6:
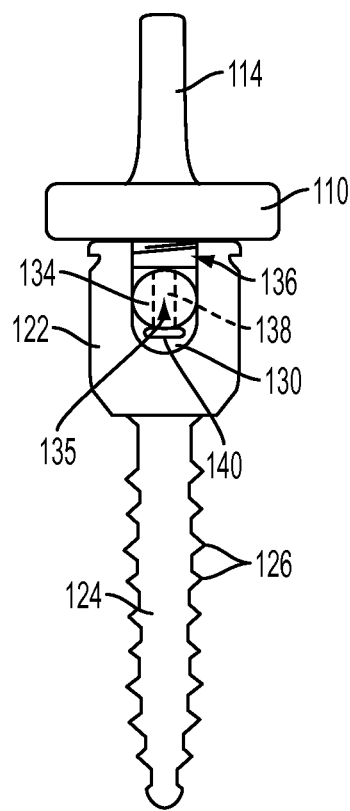
FIG. 6 is a side view of the spinal anchor of FIG. 3A attached to the child RFID tag assembly of FIG. 4.

Referring again to the embodiment of FIG. 4, the thumb grip 108 can include an annular disc 110 having a top face 112 and a protrusion 114 extending proximally therefrom and having a top face 116, although the thumb grip 108 can be configured in a variety of other ways. Generally, the child RFID tag assembly 133 can be configured to facilitate easy hand gripping thereof. The thumb grip 108 can have a distal portion 136 including a thread 136t formed thereon. The thread 136t can be configured to threadably mate with the thread formed on the surface of the recess 130 of the spinal anchor's head 122, thereby allowing the child RFID tag assembly 133 to be removably attached to the spinal anchor. The thread 136t can extend along any amount of the distal portion 136, including around an entirety of the distal portion 136 and along an entire longitudinal length of the distal portion 136, but in an exemplary embodiment, the thread 136t can extend around a minimal amount of the distal portion 136, e.g., extending down less than half the longitudinal length of the distal portion 136 and extending around more than one full circumference but less than two full circumferences around the distal portion 136, as shown in FIGS. 4 and 6. Having a minimal amount of threading can facilitate easy insertion and removal of the child RFID tag assembly 133 from the head 122 prior to use, e.g., in a hospital operating room, while still securely holding the child RFID tag assembly 133 thereto so as to help prevent accidental unthreading during shipment between different geographic locations. In an exemplary embodiment, the child RFID tag 132 can be attached to the distal portion 136 of the thumb grip 108 using a rod 138 extending distally from the distal portion 136 and passing through a bore 135 formed in a casing 134 encasing the child RFID tag 132. The casing 134 can have a size and a shape configured to be seated in the recess 130 formed in the head 122, as shown in FIG. 6. A knob 140 at a distal end of the rod 138 can have a diameter that is larger than a diameter of the bore 135 in the casing 134 so as to secure the casing 134, and hence the child RFID tag 132, between the knob 140 and the distal portion 136. The rod 138 can be movably coupled to the casing 134 such that rotation of the thumb grip 108, including the distal portion 136, as shown in FIG. 5, can rotate the rod 138 relative to the casing 134, and hence the child RFID tag 132, e.g., does not cause rotation of the casing 134 and the child RFID tag 132. The thumb grip 108 can thus assist a user in attaching and removing the child RFID tag assembly 133 from the head 122 of the spinal anchor without affecting corresponding rotation of the casing 134, the child RFID tag 132, or the spinal anchor.

The child RFID tag assembly 133 can include identification information 117 thereon that identifies the spinal anchor attached thereto, as shown in FIG. 5. In the illustrated embodiment, the top faces 112, 116 of the thumb grip 108 are labeled with the information 117, but the information 117 can be located in any one or more places on the child RFID tag assembly 133. The information 117 can include any number of identifying characteristics, including, by way of non-limiting example, information related to surgical device size, e.g., diameter, length, etc., and information related to part and lot numbers. As shown in FIG. 1, the information 117 can be visible when the spinal anchor having the child RFID tag assembly 133 attached thereto is seated in the tray 100, which can allow for manual inspection of the information 117.

In another embodiment (not shown), the child RFID tag 132 can be secured to the spinal anchor by placing the casing 134, including the child RFID tag 132, within the recess 130 of the spinal anchor's head 122 and screwing the set screw 128 into the head 122 above the casing 134 and the child RFID tag 132, without the assistance of the child RFID assembly 133, e.g., without the thumb grip 108 (including the distal portion 136) and the rod 138. The set screw 128 can therefore hold the casing 134 within the recess 130 by exerting a distal force thereon. Because the set screw 128 will typically have to be removed before implantation of the spinal anchor assembly 120 within a patient, in particular to open up the recess 130 such that it can accommodate the spinal rod 131, removing the set screw 128 will necessarily involve the removal of the child RFID tag 132, thus minimizing the risk of accidentally implanting the child RFID tag 132 within a patient.

In yet another embodiment (not shown), the thumb grip 108 can be configured to have the child RFID tag 132 attached thereto instead of having the child RFID tag 132 within the casing 134. The child RFID tag assembly in this embodiment would thus not need to include the casing 134 or the rod 138, which can simplify and/or lower cost of manufacturing.

The spinal anchor, the child RFID tag assembly 133, and/or the tray 100 can be labeled with a reminder (not shown) to remove the child RFID tag 132 or the child RFID tag assembly 133, in particular when the child RFID tag 132 is not readily visible to the naked eye, e.g., the child RFID tag 132 is seated within the spinal anchor underneath a component that would not otherwise need to be removed before implantation of the spinal anchor.

Modifications on any surgical device can similarly be configured to accommodate the child RFID tag 132, e.g., a recess formed on an exterior surface of the surgical device or a closed cavity having a "door" or lid configured to be selectively opened and closed, thus reducing the chances of accidental displacement during transportation but allowing for intentional removal, e.g. before implantation in the case of surgical implants. For surgical devices, the child RFID tag 132 can be completely embedded or enclosed in a closed cavity in any part of the surgical device, such that it is not easily removed or is not able to be removed at all. As with the parent RFID tag 107, this can help to prevent damage to the child RFID tag 132 during transport and unloading/reloading of the tray 100, and can facilitate repeated shipments of the surgical device between different geographic locations.

Like the parent RFID tag 107 discussed above, the child RFID tag 132 can be any type of RFID tag and, in an exemplary embodiment, can be configured to undergo multiple sterilizations. Each child RFID tag 132 can be the same as or different from other child RFID tags 132 attached to surgical devices seated within the tray 100. The child RFID tag 132 can thus be configured to store information similar to that discussed above regarding the parent RFID tag 107. By way of non-limiting example, the information can include information uniquely identifying the surgical device to which the child RFID tag 132 is attached and information relating to a location of the surgical device to which the child RFID tag 132 is attached in the tray 100, e.g., the child RFID tag 132 attached to the spinal anchor in row a, column 1 (see FIG. 1) indicates that the spinal anchor is seated in a position a1 of the tray 100. For surgical devices that can be reused, a child RFID tag can store use information relating to its associated surgical device, such as how many times the surgical device has been used in surgery or transported between different geographic locations, which can help trigger any necessary maintenance of the device and/or otherwise indicate if the device should be temporarily or permanently pulled out of service.

Below are discussions of various other embodiments of trays, each configured to seat a plurality of surgical devices. The various embodiments discussed below can generally be configured and used similarly to the tray 100 of FIGS. 1 and 2. Additionally, like-named elements and like-illustrated elements of trays and surgical devices discussed herein can be configured and used similar to one another.

Figure 7:
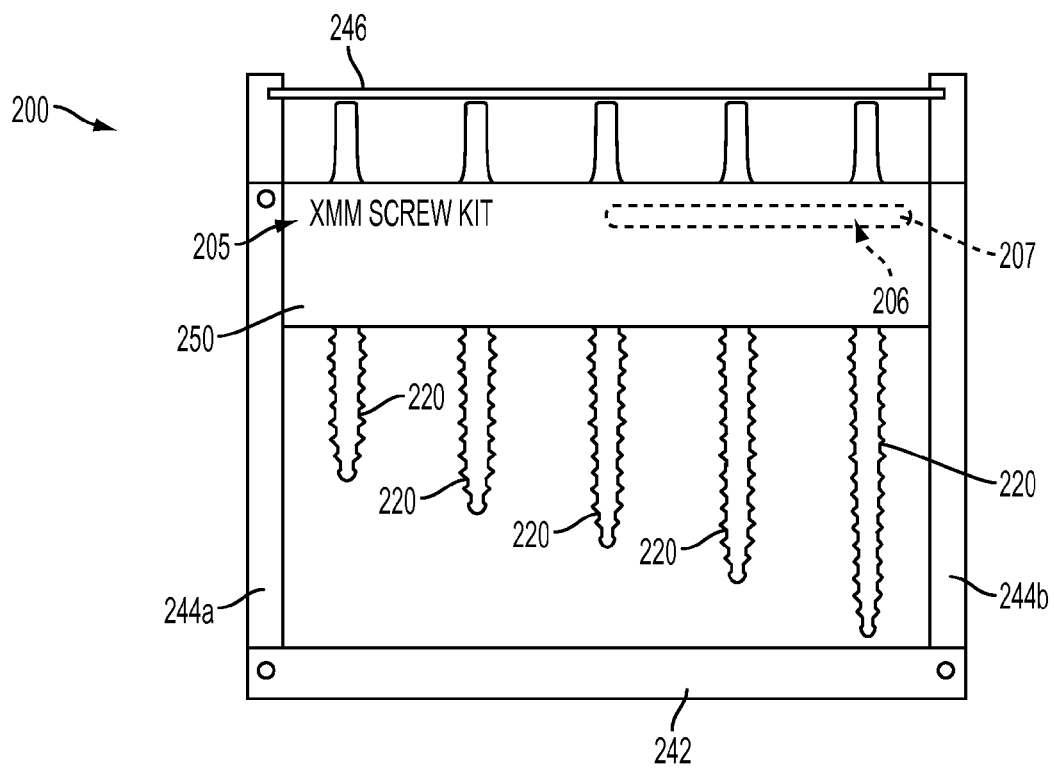
FIG. 7 is a side view of another embodiment of an implant tray having a plurality of spinal anchors seated therein, each of the spinal anchors having an RFID tag assembly attached thereto.
Figure 8:
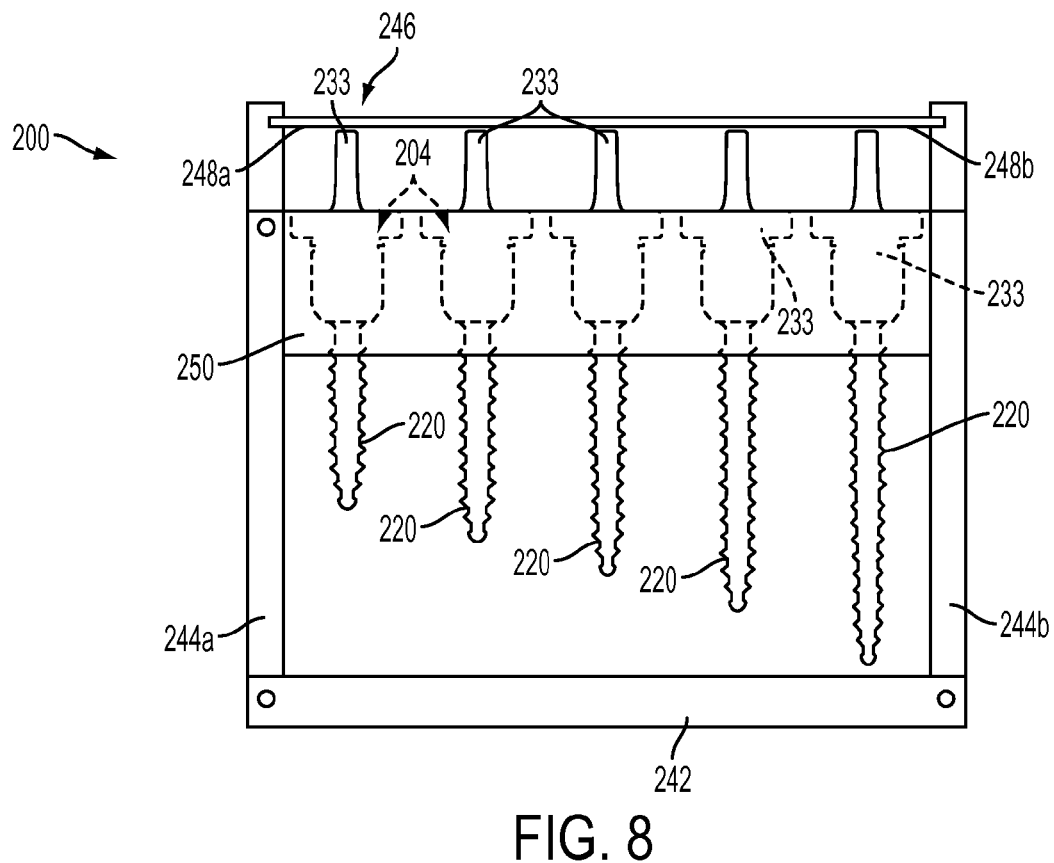
FIG. 8 is a side, partially transparent view of the implant tray of FIG. 7.

FIGS. 7 and 8 illustrate another embodiment of an implant tray 200 configured to seat a plurality of surgical devices therein. The tray 200 can include a suspended shelf 250 configured to seat a plurality of surgical devices therein. The tray 200 can include a lid 246 at a proximal end thereof, which can help reduce a likelihood of damage, loss, and/or contamination of surgical devices seated in the tray 200. To assist a user in attaching/removing or opening/closing of the lid 246, a grip or handle (not shown) can be formed on the lid 246. The suspended shelf 250 can have a plurality of recesses 204 formed therein, each of which can be configured to seat at least a portion of a surgical device, such that part of the surgical device can extend proximally, e.g., toward the lid 246, and/or distally from the shelf 250. The recesses 204 can be arranged in a single row longitudinally aligned with one another on the shelf 250, as shown, but the recesses 204 can be arranged in any other way, e.g., in any pattern, in multiple rows, etc. The shelf 250 can be suspended above a bottom panel 242 of the tray 200, such as by attachment to side panels 244a, 244b extending between the lid 246 and the bottom panel 242, and at a height that allows for surgical devices to be completely contained within the tray 200 between the lid 246 and the bottom panel 242. It will be appreciated by a person skilled in the art that the shelf 250 can be removably attached to the side panels 244a, 244b and/or can be adjusted to different heights to accommodate different types and/or sizes of surgical devices. The shelf 250 can be integral to the side panels 244a, 244b or can be movable, e.g., slideable along a slot (not shown) extending in a longitudinal direction along the side panels 244a, 244b. The tray 200 can have two additional side panels (not shown) to form a closed container, which can help protect surgical devices seated in the tray 200. The tray 200 can be labeled with information 205 in text and/or graphical format, similar to the information 105 discussed above with respect to the tray 100.

A parent RFID tag 207 can be attached to the tray 200 in any way, similar to that discussed above regarding the parent RFID tag 107 of FIGS. 1 and 2. In the illustrated embodiment, as shown in FIG. 7, the parent RFID tag 207 is embedded within the shelf 250 in a closed cavity 206 formed therein.

Although the tray 200 can be configured to seat any combination of the same or different types of surgical devices, the tray 200 in the illustrated embodiment is configured to seat a plurality of spinal anchors 220, each of which can be attached to a child RFID tag assembly 233, similar to the spinal anchor and the child RFID tag assembly 133 of FIG. 1 discussed above. As shown in FIG. 8, the shelf 250 can be configured to seat one of the spinal anchors 220 and its attached child RFID tag assembly 233 in each of the recesses 204, such that each of the spinal anchors 220 is seated fully within the tray 200, along with their associated child RFID tag assemblies 233. The tray 200 in the illustrated embodiment is configured as a kit including a plurality of the spinal anchors 220, each having a different shank length to facilitate selection of an appropriately sized spinal anchor 220 for a specific patient having a spinal procedure performed thereon. The tray 100 of FIG. 1 is similarly configured as a kit including a plurality of differently sized spinal anchors, e.g., each of the columns 1, 2, 3, 4, 5 including spinal anchors having a same shank length.

As shown, the lid 246 can be configured to slidably move in notches 248a, 248b formed in the side panels 244a, 244b along a plane substantially parallel to the bottom panel 242, thus allowing for selective access to the surgical anchors 220. It will be appreciated by a person skilled in the art that the lid 246 can be removably attached to the side panels 244a, 244b in any way, e.g., by protrusions (not shown) on the side panels 244a, 244b that slidably fit into notches (not shown) on the lid 246, by a snap-fit mechanism that allows a user to attach and remove the lid 246 by vertical movement, etc. In another embodiment, the lid 246 can be permanently attached to the side panels 244a, 244b and can be configured to open and close, e.g., with a hinge (not shown) or a sliding mechanism (not shown) having a lock configured to prevent the lid 246 from sliding out of the notches 248a, 248b entirely.

Figure 9:
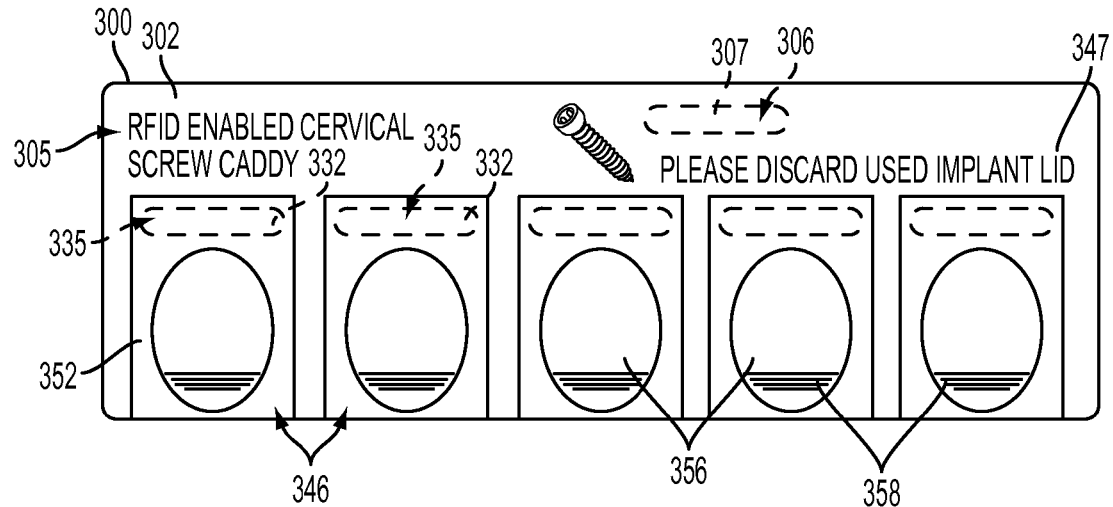
FIG. 9 is a top view of an embodiment of an implant tray having a plurality of cervical screws seated therein underneath a plurality of lids.
Figure 10:
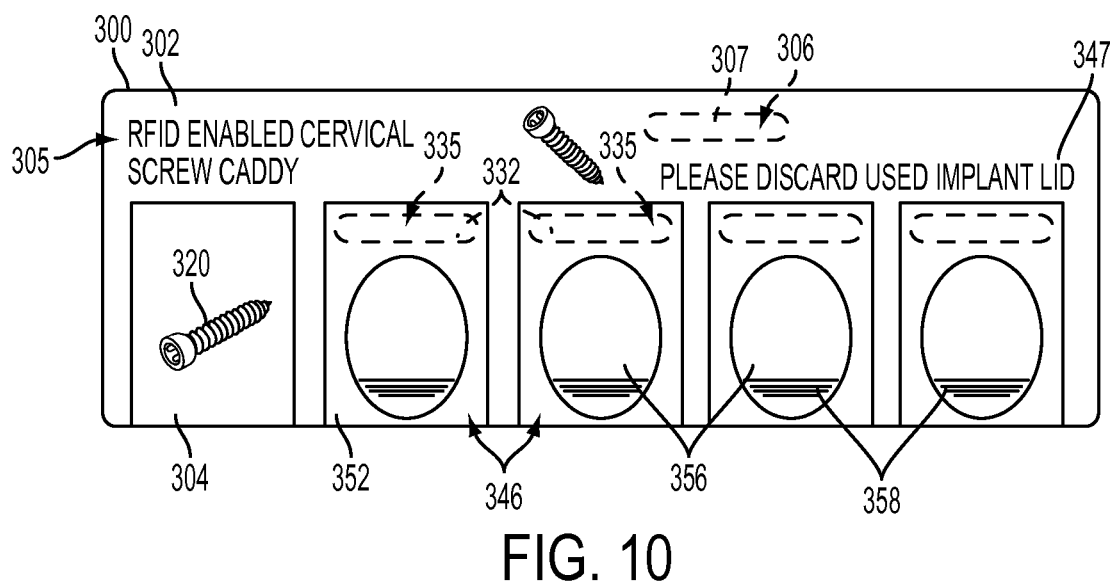
FIG. 10 is a top view of the implant tray of FIG. 9 with one of the lids removed.
Figure 11:
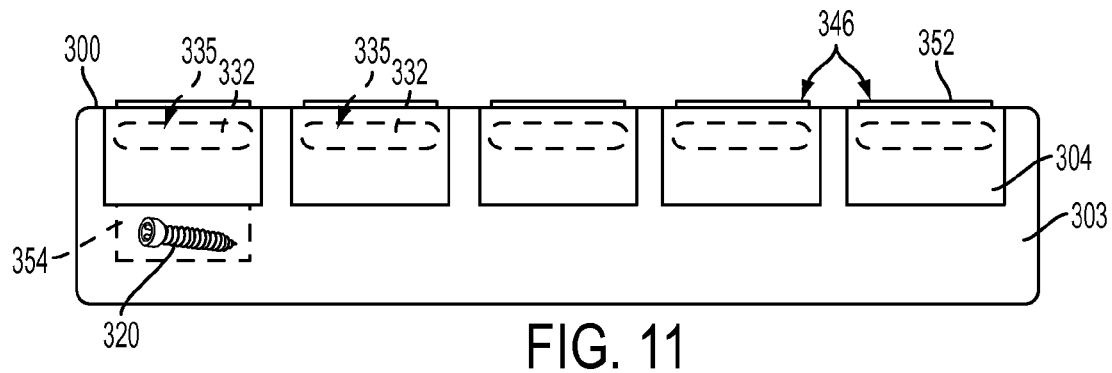
FIG. 11 is a side view of the implant tray of FIG. 9.

FIGS. 9-11 illustrate yet another embodiment of an implant tray 300 configured to seat a plurality of surgical devices therein. The tray 300 can have a plurality of removable lids 346 attached thereto. Each of the removable lids 346 can be configured to cover one of a plurality of recesses 304 formed in the tray 300 and can have a child RFID tag 332 attached thereto. As shown in FIG. 10, removing any one of the lids 346 (a left-most lid 346 is shown removed in FIG. 10) can allow a user to discard the child RFID tag 332 attached thereto and allow the user to access a surgical device seated within the newly exposed recess 304. The tray 300 can thus be particularly useful for seating and transporting surgical devices to which attachment of the child RFID tag 332 directly thereto, as in the embodiments illustrated in FIGS. 1-8, could be difficult, such as with extremely small and/or extremely delicate surgical devices. The recesses 304 can have any shape, such as a rectangular box shape, as in the illustrated embodiment, which can allow the tray 300 to accommodate a variety of surgical devices, including, by way of non-limiting example, surgical devices of a variety of shapes and sizes. Any one or more of the recesses 304 can optionally have a securing feature (not shown), such as adjustable fasteners or a light adhesive, configured to removably secure a surgical device in place within the recess 304 whether or not the lid 346 is open/on or closed/off, which can help prevent jostling and accordant damage of the surgical device prior to surgical use. The recesses 304 can be arranged in a single, longitudinally-aligned row along a top panel of the tray 300 as shown, but can be arranged in any pattern and/or in multiple rows. Similar to that discussed above, the tray 300 can be labeled with information 305 and can have a parent RFID tag 307 attached thereto, e.g., in an enclosed cavity 306 as shown.

The lids 346 can have a variety of sizes, shapes, and configurations. The lids 346 can each include a top face 352 disposed on a top panel 302 of the tray 300 and a side face 354 disposed on a side panel 303 of the tray 300, although the lids 346 can have any number of faces formed on any panels of the tray 300. Each of the lids 346 can be configured to be removed independently of the other lids 346, such as by a sliding motion parallel to the top face 352 and toward the side face 354 of the lid 346, although the lids 346 can be attached to the tray 300 by any coupling mechanism that allows for removal of its associated lid 346, e.g., by corresponding engagement features on the lid 346 and the tray 300. In an exemplary embodiment, the lids 346 can be configured to be entirely removed from the tray 300, which can allow the lids 346 to be disposed of after removal from the tray 300, thereby indicating that the surgical device exposed by the removal of the lid 346 was used in a surgical procedure and/or should be charged for as being used in a surgical procedure. The lids 346 can be configured to be non-reattachable to the tray 300 once removed therefrom, which can help facilitate billing by allowing for all removed lids 346 to indicate a billing charge. As discussed further below, the lid 346 can have a child RFID tag 332 attached thereto, which can be disposed of along with the removed lid 346. A thumb grab 356 can be formed on the top face 302 of the lid 346, which can help to provide frictional force to assist a user in slidably removing the lid 346. The thumb grab 356 can be located on any portion of the lid 346 and can take any form. In the illustrated embodiment, the thumb grab 356 includes a circular plate having a textured grip surface 358 formed on at least a portion thereof.

The child RFID tag 332 can be attached to any portion of the lid 346 in any number of ways, such as by being attached to an exterior surface of the lid 346, being seated in a recess (not shown) formed on the lid 346, or being embedded or encapsulated in a closed cavity 335 formed in the lid 346. The child RFID tag 332 can contain information that can uniquely identify the surgical device seated within the recess 304 that is covered by the lid 346 to which the child RFID tag 332 is attached. To help ensure that the lid 346 and the attached child RFID tag 332 are discarded upon removal of the surgical device seated within the recess 304 beneath the lid 346 and to assist with accounting of surgical devices removed from the tray 300, the tray 300 can be labeled with an instruction 347 to discard the lid 346 upon removal thereof from the tray 300.

The tray 300 in the illustrated embodiment is configured to seat a plurality of cervical screws 320 (see FIGS. 10 and 11). The information 305 thus identifies the tray as an "RFID Enabled Cervical Screw Caddy."

Figure 12:
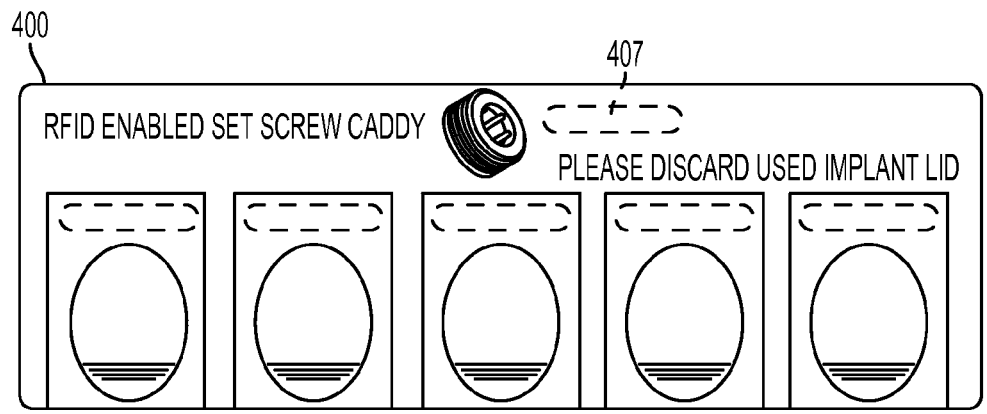
FIG. 12 is a top view of an embodiment of an implant tray having a plurality of set screws seated therein underneath a plurality of lids.
Figure 13:
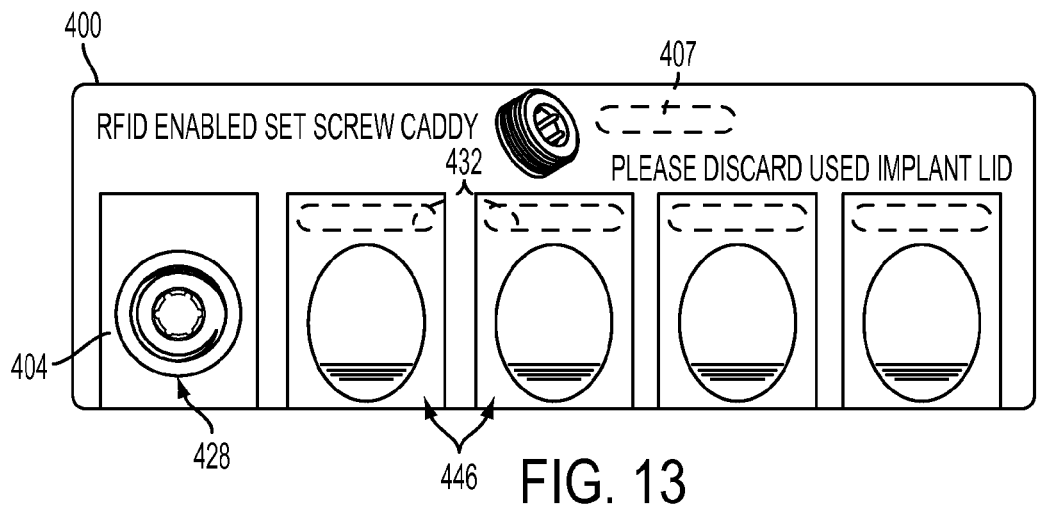
FIG. 13 is a top view of the implant tray of FIG. 12 with one of the lids removed.
Figure 14:
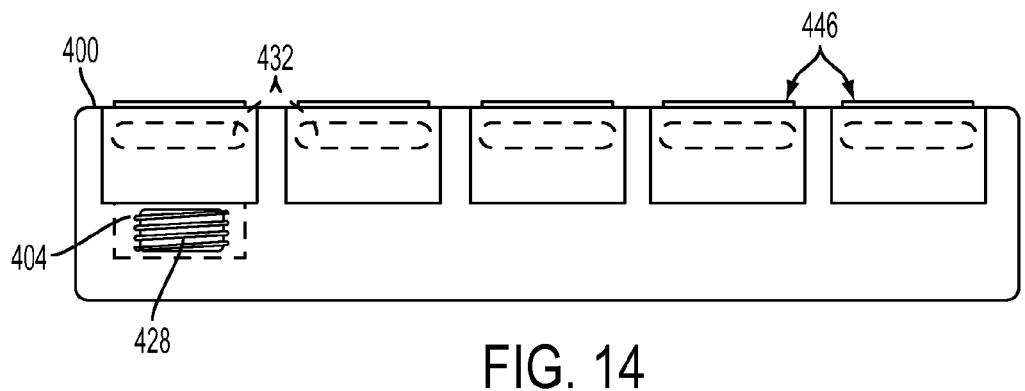
FIG. 14 is a side view of the implant tray of FIG. 12.

Another embodiment of an implant tray 400 configured to seat a plurality of surgical devices therein is illustrated in FIGS. 12-14. The tray 400 can generally be configured and used similar to the tray 300 of FIGS. 9-11, with lids 446 covering a plurality of recesses 404 formed in the tray 400, with a parent RFID tag 407 attached to the tray 400, and with child RFID tags 432 attached to surgical devices seated in the tray 400. The tray 400 in this illustrated embodiment seats a plurality of set screws 428.

Figure 15:
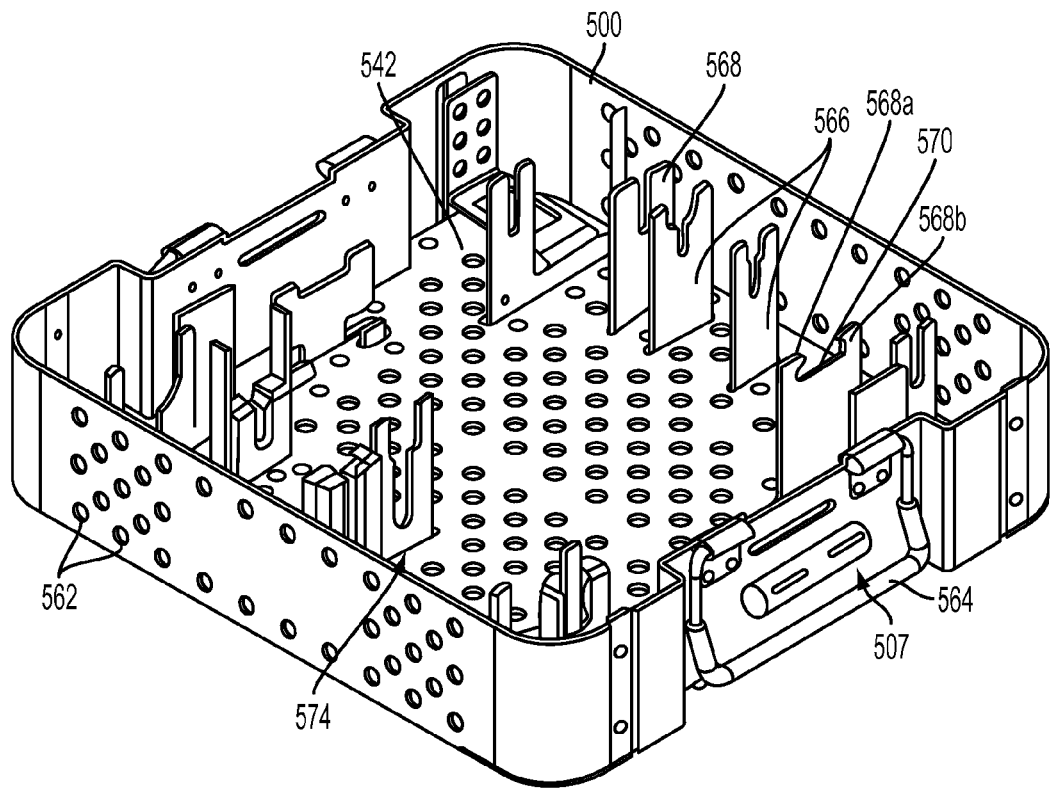
FIG. 15 is a perspective view of an embodiment of an instrument tray configured to seat a plurality of surgical devices, the instrument tray having a parent RFID tag attached thereto.

FIG. 15 illustrates another embodiment of a tray 500 configured to seat a plurality of surgical devices therein. The trays 100, 200, 300, 400 discussed above are referred to as "implant" trays and are illustrated as seating surgical implants, but the trays discussed herein can be configured to seat surgical implants other than those illustrated, e.g., rods, plates, clips, etc., and surgical accessories, e.g., sutures, gauze, etc., configured to be used once with a patient. The instrument tray 500 is configured to seat surgical devices in the form of surgical instruments, e.g., scalpels, staplers, retractors, cannulas, scissors, etc., which are configured to be used multiple times with multiple patients. The instrument tray 500 can have a plurality of apertures 562 formed therein for allowing a fluid (liquid, gas, or both) to pass therethrough, such as during sterilization and/or washing. The apertures 562 can be circular, as shown, but can be of any size and shape that does not compromise a structural integrity of the instrument tray 500, and can be arranged in any pattern along surfaces of the instrument tray 500. The instrument tray 500 can have one or more handles 564 attached thereto, which can facilitate carrying and other transportation of the instrument tray 500. The instrument tray 500 can have a variety of shapes, e.g., to fit into a storage area or an autoclave, such as a substantially square shape as in the illustrated embodiment.

A parent RFID tag 507 can be attached to any part of the tray 500, in any of a variety of ways. The parent RFID tag 507 can be either removably or permanently attached to any portion of the tray 500, as mentioned above, including to the handle(s) 564 attached to the tray 500. Also as mentioned above, the parent RFID tag 507 can be configured to undergo multiple sterilizations and/or to be reprogrammable, and can be configured to store information relating to the tray 500 and/or to surgical devices (not shown) seated therein. The parent RFID tag 507 is shown in the illustrated embodiment as being attached to an external surface of the tray 500 by being snap fit thereon via a casing enclosing the parent RFID tag 507.

As shown, the tray 500 can be configured to seat a plurality of the same or different types of surgical devices. The tray 500 can include a plurality of supports 566 configured to support various portions of surgical devices. By way of non-limiting example, each of the supports 566 can have at least one prong 568 formed on an upper end of the support 566, such that the surgical device can be seated within a recess 570 formed by adjacent prongs 568a, 568b on the same support 566. A surgical device can be seated in only one of the supports 566, or the surgical device can be seated in a plurality of the supports 566, with each of the supports 566 configured to receive a particular portion of the surgical device. The supports 566 can be formed on or fixed onto a bottom panel 542 of the tray 500, or the supports 566 can be removably inserted into one of a plurality of support slots 574 formed in, e.g., the bottom panel 542 of the tray 500 such that different supports 566 can be selectively removed and attached to accommodate different surgical devices. The supports 566 can be of any width and any height, and the prongs 568a, 568b can similarly have any dimension. The surgical devices can be removably secured within the recesses 570 by, e.g., snap-fit, a light adhesive, interference fit, etc.

Figure 16:
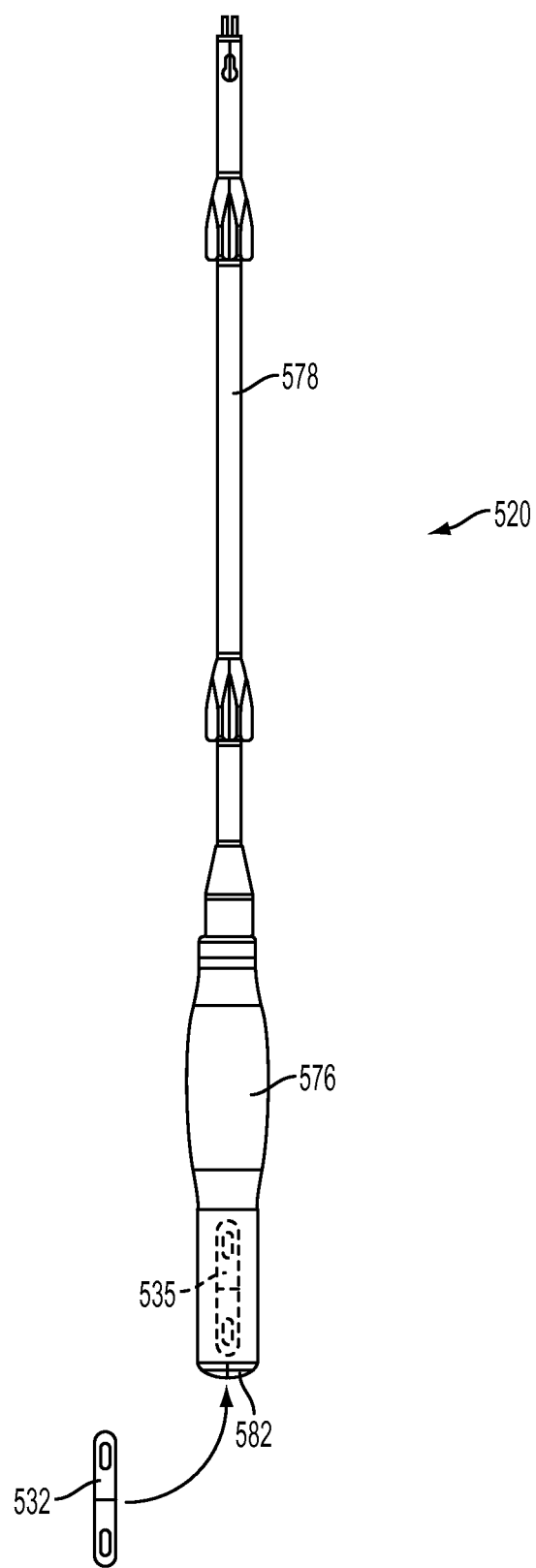
FIG. 16 is a side view of an embodiment of a surgical instrument having a child RFID tag attached thereto.

One embodiment of a surgical instrument 520, e.g., a driver configured to drive a spinal anchor into bone, that can be seated in the instrument tray 500 is shown in FIG. 16. The surgical instrument 520 can include a handle 576 and an elongate shaft 578 extending distally from the handle 576.

The surgical instrument 520 can have a child RFID tag 532 attached thereto. The child RFID tag 532 can be attached to the surgical instrument 520 in a variety of ways, as discussed above. As in the illustrated embodiment, the child RFID tag 532 can be embedded in the handle 576 in a closed cavity 535 formed therein. FIG. 16 shows the child RFID tag 532 outside of the cavity 535 for clarity. Having the child RFID tag 532 attached to a portion of the surgical instrument 520 typically not inserted into a patient's body, e.g., in a handle, can help protect the child RFID tag 532 from damage during use of the surgical instrument 520, e.g., to protect the child RFID tag 532 from exposure to liquid at a surgical site. The handle 576 can include a removable cap 582 attached to a proximal end of the handle 576 that can be configured to be removably and replaceably attached thereto to provide access to the child RFID tag 532, e.g., for technology upgrades, maintenance, replacement, etc. The removable cap 582 can have any size, shape, and configuration and can be attached to the handle 576 in any way, e.g., matable threads, snap fit, interference fit, etc.

Figure 17:
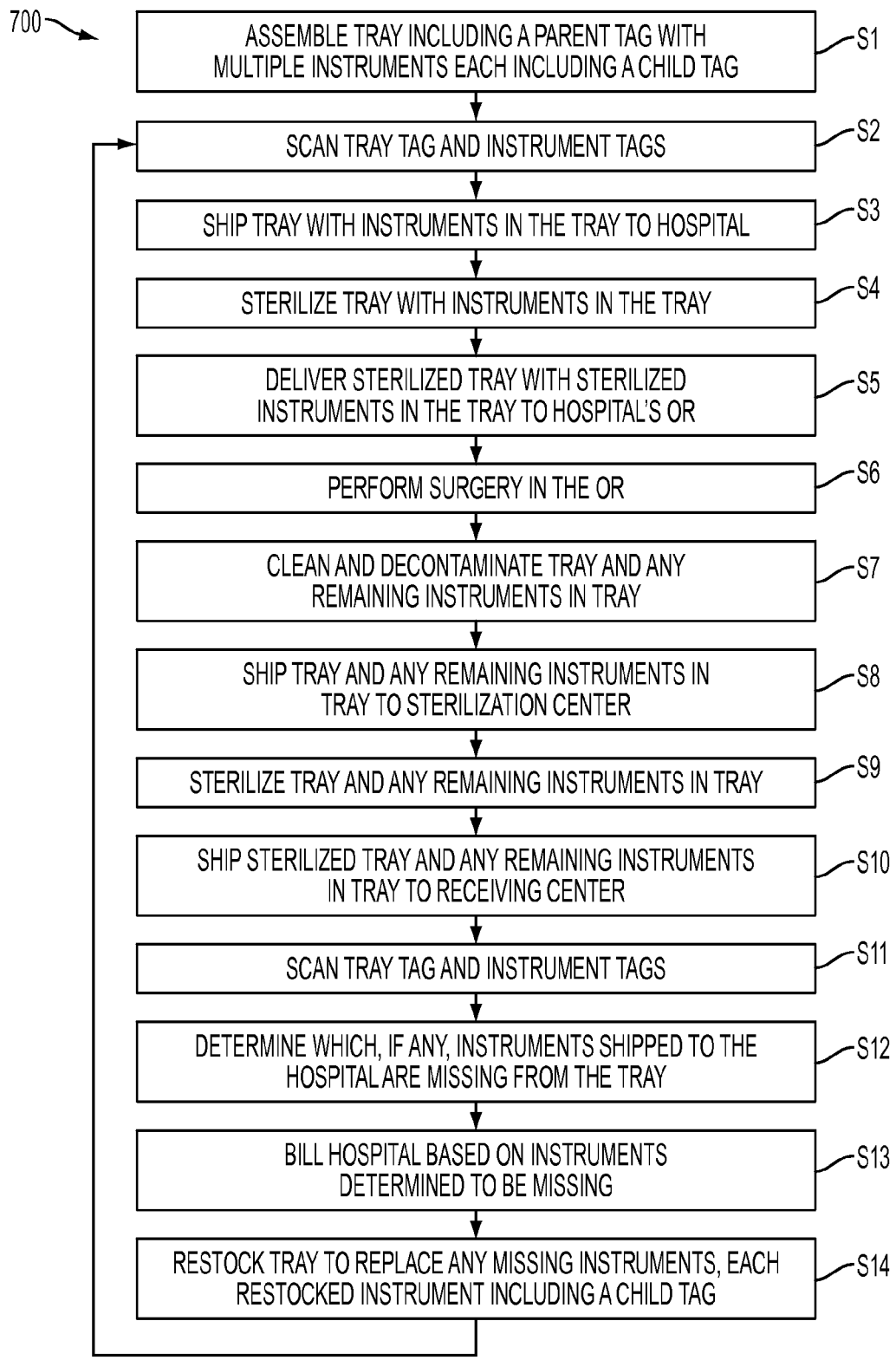
FIG. 17 is a flowchart showing one embodiment of a process of surgical device distribution.

As mentioned above, trays having parent RFID tags attached thereto and having surgical device(s) seated therein, which have child RFID tags attached thereto, can be transported between different locations to allow the surgical device(s) to be available for use in a surgical procedure. One embodiment of a process 700 of surgical device distribution is shown in FIG. 17. It will be appreciated by a person skilled in the art that the process 700 shown in FIG. 17 is an illustrative, non-limiting example of a process that can be used in distributing trays and surgical devices.

In the process 700, a tray can be assembled (s1) either manually, e.g., by a representative of a medical device company, or by using an automated method, e.g., by an assembly line. The assembly (s1) can include seating a plurality of surgical devices in the tray. A child RFID tag, which can be contained within a child RFID tag assembly, can be attached to each of the surgical devices seated in the tray, either prior or subsequent to seating of the surgical devices in the tray, if the child RFID tags are not already attached thereto, e.g., permanently embedded therein. In an exemplary embodiment, every recess 104 formed in the tray and/or every support mated to the tray can have a surgical device seated therein, although any number of the recesses and/or supports can be left empty, such as to reflect a specifically ordered number of surgical devices for a specific surgical procedure. Assembling (s1) the tray can include attachment of a parent RFID tag to the tray in any number of ways, as mentioned above, if the parent RFID tag is not already attached to the tray. As mentioned above, each child RFID tag can be programmed to store information that can uniquely identify the surgical device to which it is attached, and the parent RFID tag can be programmed to store a "master" list that can uniquely identify all of the surgical devices seated within the tray. The programming of the parent RFID tag and of the child RFID tag(s) can both occur prior to assembling (s1) the tray, subsequent to assembling (s1) the tray, or a combination thereof.

The parent RFID tag and the child RFID tag(s) can be scanned (s2), e.g., manually by the representative using an external reading device, or automatically, e.g., using an external reading device mounted to an tray conveyer belt. The scan (s2) can also optionally include manual inspection of information on the tray and/or information on the surgical devices and/or child RFID tag assembly/ies. The results of the scan (s2) can indicate that all of the necessary surgical devices are seated within the tray, such as by manual comparison of the scan of the parent RFID tag with the scan of the child RFID tag(s) or by using an automated checking method, e.g., a comparison process run on a computer, as will be appreciated by a person skilled in the art. The scans can optionally be recorded or stored in a secure location for, e.g., comparison with subsequent scans of the parent RFID tag and the child RFID tag(s), verification that all the correct surgical devices were initially seated in the tray prior to shipment, etc.

The tray, along with all of the surgical devices seated therein, can be shipped (s3) to an order destination, such as a hospital or other medical facility, in any way. The tray and the surgical devices seated therein can be sterilized (s4), such as at the order destination. The tray and the surgical devices can be sterilized (s4) in any way, as will be appreciated by a person skilled in the art, such as beta or gamma radiation, ethylene oxide, steam, and a liquid bath (e.g., cold soak). Once sterilized (s4), the tray and the surgical devices seated therein can be delivered (s5) to an operating room, or other appropriate destination, for use in surgery. Medical personnel can then perform (s6) the surgery, during which any number of the surgical devices seated in the tray can be removed therefrom and used in performing the surgery. After the surgery is performed (s6), the tray and any remaining surgical devices seated therein can be cleaned and decontaminated (s7), in any way, as will be appreciated by a person skilled in the art. Alternatively, the surgery may not be performed, e.g., if the patient's circumstances have changed such that the surgery is canceled. The tray and any remaining devices seated therein can be, but need not be, cleaned and decontaminated (s7) after the decision is made to not perform the surgery. Similarly, the tray and any devices seated therein may not yet have been sterilized before the decision is made to not perform the surgery, in which case sterilization thereof can be, but need not be, performed.

Post-surgery, or after a determination that surgery using the tray and the surgical device(s) seated therein will not be performed, the tray and any remaining surgical devices seated therein can be shipped (s8) to a sterilization center, where the tray and any remaining surgical devices seated therein can be sterilized (s9) in any way and shipped (s10) to a receiving center. At the receiving center, the parent RFID tag and any remaining child RFID tags can be scanned (s11), manually and/or automatically. The scan (s11) of all of the child RFID tags attached to any surgical devices remaining in the tray can produce information, e.g., child information, uniquely identifying the surgical devices remaining in the tray. The scan (s11) of the parent RFID tag can produce "master" information, e.g., a "master" list, which can include information uniquely identifying all of the surgical devices in the tray at the time of the earlier scan (s2). In some embodiments, the scan (s11) of the parent RFID tag may not produce a master list but instead produce information that can allow access to a previously stored master list, e.g., by looking up a previously stored master list for a unique identification code identified via the scan (s11). Following the scan (s11), a determination (s12) of which surgical devices have been removed from the tray can be performed, either manually, e.g., by the representative, or by using an automated method, e.g., an electronic comparison performed by a processor (e.g., a central processing unit (CPU) of a computer), and can involve comparing the "master" list with the information gleaned from the scan (s11) of each of the remaining child RFID tags. The determining (s12) can produce an accurate result even if one or more of the surgical devices were simply moved to different positions within the tray. Using FIG. 1 as a non-limiting example, if the spinal anchor originally seated in position a1 were removed and the spinal anchor originally seated in position a2 were moved to position a1, comparison of the post-surgery scan (s11) would still result in a determination that the spinal anchor in the position a1 was the only surgical device removed from the tray 100.

Referring again to FIG. 17, having determined (s12) which of the surgical devices, if any, were removed from the tray, a customer, e.g., the hospital, can be billed (s13) for the surgical devices that were removed from the tray. As will be appreciated by a person skilled in the art, the customer can be billed for additional costs, e.g., shipping charges, labor, etc.

The tray can be restocked (s14) to replace any missing surgical devices, with similar or different surgical devices. The restocking (s14) can be performed in any number of ways, as will be appreciated by a person skilled in the art, such as manually by the representative, or by using an automated method such as an assembly line. Each of the newly added surgical devices can have a child RFID tag attached thereto. The parent RFID tag attached to the tray can optionally be removed and reattached, or the parent RFID tag can remain attached to the tray and can be reprogrammed with a new "master" list of information uniquely identifying each of the surgical devices seated in the tray after the restocking (s14). The distribution process 700 can then be repeated any number of times by scanning (s2) the tray's parent RFID tag and the surgical devices' child RFID tags.

As the distribution process 700 can be repeated any number of times, the same tray, the same parent RFID tag, the same child RFID tags and the same surgical devices can experience multiple distribution cycles. The exemplary distribution process 700 can be used with any surgical device carrying apparatus and any number and combination of surgical devices, either same or different, seated therein. The process 700 can vary in different cycles of the process, e.g., as to the geographical location to which the tray is shipped. The process 700 can be modified in a variety of ways, such as to provide additional scans of the parent RFID tag attached to the tray, e.g., after the tray is shipped to a hospital and/or after decontamination following surgery, and such as billing the customer once every several distribution cycles, e.g., after multiple surgeries, rather than once at the end of each distribution cycle.

The surgical devices disclosed herein can be designed to be disposed of after a single use, or they can be designed to be used multiple times. In either case, however, the surgical device can be reconditioned for reuse after at least one use. Reconditioning can include any combination of the steps of disassembly of the surgical device, followed by cleaning or replacement of particular pieces, and subsequent reassembly. In particular, the surgical device can be disassembled, and any number of the particular pieces or parts of the surgical device can be selectively replaced or removed in any combination. Upon cleaning and/or replacement of particular parts, the surgical device can be reassembled for subsequent use either at a reconditioning facility, or by a surgical team immediately prior to a surgical procedure. Those skilled in the art will appreciate that reconditioning of a surgical device can utilize a variety of techniques for disassembly, cleaning/replacement, and reassembly. Use of such techniques, and the resulting reconditioned surgical device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A radio frequency identification (RFID) assembly, comprising:
    a thumb grip, comprising:
        an annular disc including a proximal surface and a distal surface;
        a protrusion extending from the proximal surface; and
        a threaded distal portion extending from the distal surface; and
    a RFID tag rotatably secured to the threaded distal portion,
    wherein the RFID tag is disposed within a casing having a bore extending therethrough,
    wherein the threaded distal portion includes a rod extending from a distal end of the threaded distal portion, and
    Wherein the rod is disposed within the bore of the casing to rotatably secure the RFID tag to the thumb grip.

2. The RFID assembly of claim 1, wherein
a knob having a diameter greater than the bore is disposed at the distal most end of the rod and is configured to retain the RFID tag on the rod.

3. The RFID assembly of claim 1, wherein the thumb grip and the RFID tag are non-removably mated to one another such that they can be installed in a surgical instrument or implant as a single assembly.

4. The RFID assembly of claim 1, wherein the threaded distal portion is cylindrical and includes threads that extend around the threaded distal portion more than one full rotation but less than two full rotations.

5. A radio frequency identification (RFID) assembly, comprising:
    a thumb grip, comprising,
        an annular disc including a proximal surface and a distal surface;
        a protrusion extending from the proximal surface; and
        a threaded distal portion extending from the distal surface; and
    a RFID tag rotatably secured to the threaded distal portion,
    wherein the assembly is configured to be inserted in a surgical instrument or implant, and
    wherein the RFID tag stores information uniquely identifying the surgical instrument or implant, how many times the surgical instrument or implant has been sterilized, and how many times the surgical instrument or implant has been transported between different geographical locations.

6. The RFID assembly of claim 5, wherein the surgical instrument or implant is a bone anchor.

7. The RFID assembly of claim 1, wherein:
    at least one of the proximal surface of the annular disc and a surface of the protrusion includes visually indentifying information of a surgical instrument or implant.

8. A method of securing a radio frequency identification (RFID) assembly within a surgical instrument or implant, comprising:
    gripping a thumb grip having a proximal gripping portion, an annular disc, and a distal shaft to which an RFID tag is rotatably mated;
    inserting the RFID tag and at least a portion of the distal shaft within a recess of a surgical instrument or implant;
    rotating the thumb grip relative to the surgical instrument or implant and relative to the RFID tag to secure the thumb grip and the RFID tag within the surgical instrument or implant; and
    storing information on the RFID tag including at least one of how many times the surgical instrument or implant has been sterilized and how many times the surgical instrument or implant has been transported between different geographical locations.

9. The method of claim 8, wherein rotating the thumb grip comprises:
    rotating the thumb grip at least a full rotation and at most less than two full rotations to secure the thumb grip and the RFID tag within the surgical instrument or implant.

10. The method of claim 8, further comprising:
    storing information uniquely identifying the surgical instrument or implant on the RFID tag.

11. The method of claim 8, further comprising:
    labeling at least one of a top surface of the annular disc or a proximal face of the proximal gripping portion with indentifying information of the surgical instrument or implant.

12. The method of claim 11, wherein the thumb grip further includes a threaded distal portion extending distally from the annular disc and the distal shaft extends from the threaded distal portion.

13. The method of claim 12, further comprising:
    threading the threaded distal portion of the thumb grip into the recess formed in the surgical instrument or implant.

14. The method of claim 8, further comprising:
    inserting the RFID tag within a casing, the casing being rotatably secured to the thumb grip.

15. A radio frequency identification (RFID) tag assembly, comprising:
    a RFID tag case including:
        a length and a width;
        a bore disposed at a midpoint along the length of the case; and
        a RFID tag disposed within the case; and a thumb grip assembly including:
- a disc including a top surface having a generally rectangular protrusion extending proximally therefrom and bottom surface having a cylindrical protrusion extending distally therefrom;
- a rod extending distally from the cylindrical protrusion;
- a knob disposed at a distal most end of the rod; and
- a knob having a diameter that is larger than the diameter of the bore, wherein the RFID tag case is rotatably secured on a distal end of the thumb grip assembly.

16. The RFID tag assembly of claim 15, wherein the length of the RFID tag case is larger than the diameter of the disc.

* * * * *